(12) United States Patent
Lin et al.

(10) Patent No.: US 11,123,386 B2
(45) Date of Patent: Sep. 21, 2021

(54) **FERMENTATION PRODUCT OF *PUNICA GRANATUM* AND USES THEREOF**

(71) Applicant: TCI CO., LTD., Taipei (TW)

(72) Inventors: Yung-Hsiang Lin, Taipei (TW); Wei Hsiu Chuang, Taipei (TW)

(73) Assignee: TCI CO., LTD., Taipei (TW)

( * ) Notice: Subject to any disclaimer, the term of this patent is extended or adjusted under 35 U.S.C. 154(b) by 371 days.

(21) Appl. No.: 16/206,123

(22) Filed: Nov. 30, 2018

(65) Prior Publication Data

US 2019/0224259 A1 Jul. 25, 2019

Related U.S. Application Data

(60) Provisional application No. 62/671,536, filed on May 15, 2018, provisional application No. 62/619,575, filed on Jan. 19, 2018.

(30) Foreign Application Priority Data

Aug. 30, 2018 (TW) ................................ 107130400

(51) Int. Cl.
| | | |
|---|---|---|
| *A61K 36/00* | (2006.01) | |
| *A61K 36/185* | (2006.01) | |
| *A61K 8/9789* | (2017.01) | |
| *A61Q 19/08* | (2006.01) | |
| *A61P 17/00* | (2006.01) | |
| *A23L 33/105* | (2016.01) | |
| *A61K 36/064* | (2006.01) | |

(52) U.S. Cl.
CPC .......... *A61K 36/185* (2013.01); *A23L 33/105* (2016.08); *A61K 8/9789* (2017.08); *A61K 36/064* (2013.01); *A61P 17/00* (2018.01); *A61Q 19/08* (2013.01); *A23V 2002/00* (2013.01); *A23V 2200/318* (2013.01); *A23V 2250/21* (2013.01); *A61K 2236/19* (2013.01); *A61K 2236/331* (2013.01); *A61K 2800/85* (2013.01)

(58) Field of Classification Search
None
See application file for complete search history.

(56) References Cited

U.S. PATENT DOCUMENTS

2011/0142990 A1* 6/2011 Jacob .................. A61K 36/185
426/51

* cited by examiner

*Primary Examiner* — Qiuwen Mi
(74) *Attorney, Agent, or Firm* — Chieh-Mei Wang

(57) ABSTRACT

The present disclosure provides a fermentation product of *Punica granatum* and methods for regulating expression of MMP gene, TIMP gene and COL4A4 gene, promoting collagen production, and anti-aging by using the fermentation product of *Punica granatum*.

7 Claims, 15 Drawing Sheets

Specification includes a Sequence Listing.

```
                       SEQUENCE LISTING

<160> NUMBER OF SEQ ID NOS: 8

<210> SEQ ID NO 1
   <211> LENGTH: 22
   <212> TYPE: DNA
   <213> ORGANISM: Artificial Sequence
   <220> FEATURE:
   <223> OTHER INFORMATION: synthetic primer

<400> SEQUENCE: 1
gatacccctt tgacggtaag ga                                                   22

<210> SEQ ID NO 2
   <211> LENGTH: 21
   <212> TYPE: DNA
   <213> ORGANISM: Artificial Sequence
   <220> FEATURE:
   <223> OTHER INFORMATION: synthetic primer

<400> SEQUENCE: 2
ccttctccca aggtccatag c                                                    21

<210> SEQ ID NO 3
   <211> LENGTH: 21
   <212> TYPE: DNA
   <213> ORGANISM: Artificial Sequence
   <220> FEATURE:
   <223> OTHER INFORMATION: synthetic primer

<400> SEQUENCE: 3
agagtgtctg cggatacttc c                                                    21

<210> SEQ ID NO 4
   <211> LENGTH: 21
   <212> TYPE: DNA
   <213> ORGANISM: Artificial Sequence
   <220> FEATURE:
   <223> OTHER INFORMATION: synthetic primer

<400> SEQUENCE: 4
ccaacagtgt aggtcttggt g                                                    21

<210> SEQ ID NO 5
   <211> LENGTH: 19
   <212> TYPE: DNA
   <213> ORGANISM: Artificial Sequence
```

```
<220> FEATURE:
<223> OTHER INFORMATION: synthetic primer

<400> SEQUENCE: 5
ctgggctaca ctgagcacc                                                   19

<210> SEQ ID NO 6
<211> LENGTH: 21
<212> TYPE: DNA
<213> ORGANISM: Artificial Sequence
<220> FEATURE:
<223> OTHER INFORMATION: synthetic primer

<400> SEQUENCE: 6
aagtggtcgt tgagggcaat g                                                21

<210> SEQ ID NO 7
<211> LENGTH: 21
<212> TYPE: DNA
<213> ORGANISM: Artificial Sequence
<220> FEATURE:
<223> OTHER INFORMATION: synthetic primer

<400> SEQUENCE: 7
agataagggt ccaactggtg t                                                21

<210> SEQ ID NO 8
<211> LENGTH: 23
<212> TYPE: DNA
<213> ORGANISM: Artificial Sequence
<220> FEATURE:
<223> OTHER INFORMATION: synthetic primer

<400> SEQUENCE: 8
acctttaacg gcacctaaaa tga                                              23
```

FERMENTATION PRODUCT OF *PUNICA GRANATUM* AND USES THEREOF

CROSS-REFERENCE TO RELATED APPLICATION

This application claims priority of U.S. provisional patent application No. 62/619,575, filed on Jan. 19, 2018, U.S. provisional patent application No. 62/671,536, filed on May 15, 2018, and Taiwan patent application No. 107130400, filed on Aug. 30, 2018, the content of which is incorporated herein in its entirety by reference.

BACKGROUND OF THE INVENTION

1. Field of the Invention

The present invention relates to a fermentation product of *Punica granatum* and methods for regulating expression of MMP gene, TIMP gene and COL4A4 gene, promoting collagen production, and anti-aging by using the fermentation product of *Punica granatum*.

2. The Prior Art

Skin tissue is composed of epidermis, dermis and subcutaneous tissue. The dermis contains a large amount of collagen and hyaluronic acid, which is closely related to the water retention and elasticity of the skin. There is aging, rough skin or wrinkles in the human skin due to age, physiological factors or environmental factors. For example, the skin of normal young people has certain elasticity and tension. After the muscle of expression is relaxed, the skin will quickly recover, causing the wrinkles to disappear. But after the middle age, the skin begins to age significantly, the skin becomes thinner, harder, drier, and the tension is reduced. Reduced dermal collagen, elastic fiber degeneration and fracture reduce the tension and elasticity of the skin. Therefore, after the muscle of expression is relaxed, the skin cannot quickly recover, and the wrinkles are formed over time. As the age increases, the skin and subcutaneous tissue are more relaxed, and the atrophy or loss of the facial supporting tissue, as well as the muscles are soft, the skin will fall under the action of gravity, forming serious wrinkles. Rough skin is caused by external factors such as dryness, ultraviolet rays, detergents or chemicals, and internal factors such as disorders of hormone balance, and accompanied by the decrease of the barrier function of the stratum corneum, the decrease of the water content of the stratum corneum, hypermetabolic turnover of epidermis, the generation of scales and the roughening of the keratin. Therefore, if the cells on the skin lose their elasticity and moisturizing function, they may cause wrinkles, dryness and loss of luster on the skin.

At present, the methods commonly used to solve skin problems are using pharmaceuticals, skin care products applied to the skin surface, or orally taking health foods with anti-aging effects. However, most of the conventional pharmaceuticals, skin care products and health foods are made of chemical ingredients. Long-term use is not only harmful to human health, but these products are often expensive and not affordable to the users.

In order to solve the above problems, those skilled in the art urgently need to develop novel pharmaceuticals, skin care products or food products having the effects on promoting collagen production and anti-aging for the benefit of a large group of people in need thereof.

SUMMARY OF THE INVENTION

A primary objective of the present invention is to provide a fermentation product of *Punica granatum*, obtained by a process comprising the following steps: (a) extracting the *Punica granatum* with water to obtain a *Punica granatum* extract; and (b) sequentially fermenting the *Punica granatum* extract with *Saccharomyces cerevisiae* and *Lactobacillus plantarum* to obtain a first fermentation product of *Punica granatum*; wherein the *Saccharomyces cerevisiae* has a concentration ranging from 0.01% to 0.5%, and the *Lactobacillus plantarum* has a concentration ranging from 0.01% to 0.25%.

According to an embodiment of the present invention, a fermentation time of the *Saccharomyces cerevisiae* ranges from 1 to 2 days, and a fermentation time of the *Lactobacillus plantarum* ranges from 1 to 3 days.

According to an embodiment of the present invention, the first fermentation product of *Punica granatum* is further fermented with *Acetobacter aceti* to obtain a second fermentation product of *Punica granatum*.

According to an embodiment of the present invention, the *Acetobacter aceti* has a concentration ranging from 1% to 20%.

According to an embodiment of the present invention, a fermentation time of the *Acetobacter aceti* ranges from 14 to 21 days.

According to an embodiment of the present invention, an extraction temperature of the process ranges from 50° C. to 100° C., and an extraction time of the process ranges from 0.5 to 3 hours.

Another objective of the present invention is to provide a method for regulating expression of matrix metalloproteinase (MMP) gene, tissue inhibitor of matrix metalloproteinase (TIMP) gene, and collagen type IV alpha 4 chain (COL4A4) gene, comprising administering to a subject in need thereof a composition comprising an effective amount of the aforesaid first fermentation product of *Punica granatum*.

According to an embodiment of the present invention, the first fermentation product of *Punica granatum* is further fermented with *Acetobacter aceti* to obtain a second fermentation product of *Punica granatum*.

According to an embodiment of the present invention, the composition is in the form of a pharmaceutical composition, a food product, or a cosmetic composition.

According to an embodiment of the present invention, the MMP gene is MMP2 gene.

According to an embodiment of the present invention, the TIMP gene is TIMP1 gene.

Another objective of the present invention is to provide a method for promoting collagen production and anti-aging, comprising administering to a subject in need thereof a composition comprising an effective amount of the aforesaid first fermentation product of *Punica granatum*.

According to an embodiment of the present invention, the composition is in the form of the cosmetic composition.

According to an embodiment of the present invention, the first fermentation product of *Punica granatum* is further fermented with *Acetobacter aceti* to obtain a second fermentation product of *Punica granatum*.

According to an embodiment of the present invention, the composition is in the form of the food product.

In summary, the fermentation product of *Punica granatum* has the effect on regulating the expression of the MMP gene, the TIMP gene and the COL4A4 gene, releasing total polyphenols of the *Punica granatum* by the microbial fermentation process, increasing the antioxidant and skin care functions, promoting collagen production, reducing pigment production and accumulation, enhancing skin firmness, anti-aging and smoothing wrinkles.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

Figure 1:
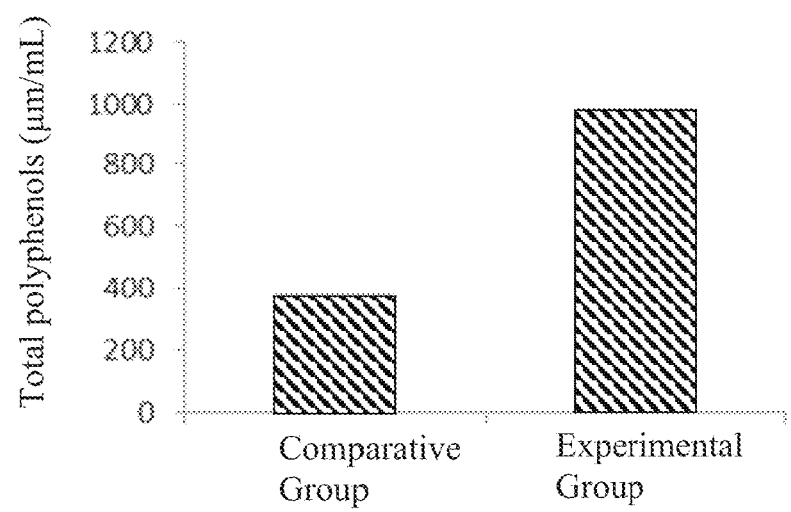
FIG. 1 is a schematic diagram showing the total polyphenol content detection of the fermentation product of *Punica granatum* of the present invention.

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

Statistical analysis was performed using Excel. Data are expressed as mean±standard deviation (SD), and the difference between each group is analyzed by the Student's t-test.

According to the present invention, *Punica granatum*, English name Pomegranate, is a deciduous shrub in the family Lythraceae and the genus *Punica*. The leaves are opposite or nearly clustered, and the appearance is oblong or obovate. The flowers are born from the top or the axillary. The berry is nearly spherical, reddish with fleshy rind. The production areas are mainly distributed in Iran, the Himalayas in northern India, China, the United States, and the Mediterranean region. The main areas of utilization of *Punica granatum* are leaves, flowers, peels, and roots. In Chinese folk medicine, the peel of *Punica granatum* is used to treat epistaxis, otitis media, traumatic bleeding, menstrual disorders, leucorrhea, toothache, vomiting blood, chronic diarrhea, long-term sputum, blood in the stool, rectal prolapse, slippery sperm, uterine bleeding, vaginal discharge, insects and abdominal pain, and scabies. In addition, *Punica granatum* has antiviral, antibacterial, antifungal and anti-cancer effects, and can be used to improve cardiovascular health, prevent diabetes, relieve menopausal symptoms, improve erectile dysfunction, and treat Alzheimer's disease and rheumatoid arthritis.

As used herein, the term "*Punica granatum* juice" means the juice produced by the fruit of *Punica granatum* comprising peel, pulp (i.e., edible portion) and seed.

As used herein, the term "water extract of *Punica granatum*" means that the *Punica granatum* juice and water are extracted at a specific time and temperature in a ratio of 1:5 to 1:10 (w/w).

As used herein, the term "anti-aging" means preventing or slowing the aging of the appearance of human skin, such as the production of wrinkles and loss of elasticity. The extent to which this is achieved is determined by a number of factors known to those skilled in the art, such as the general condition of the consumer, age, and gender.

As used herein, the terms "culturing" and "cultivation" can be used interchangeably.

According to the present invention, operational procedures and parameter conditions relating to fermentation culturing are within the scope of professional literacy and routine techniques of those skilled in the art.

As used herein, the terms "*Saccharomyces cerevisiae*", "*Lactobacillus plantarum*" and "*Acetobacter aceti*" are intended to encompass those easily obtained by those skilled in the art, respectively. For example, those microorganisms can be available from domestic or foreign depository, or isolated and purified from natural sources by the microorganism separation process conventionally used in the art.

According to the present invention, the pharmaceutical composition can be manufactured to a form suitable for parenteral or topical administration, using techniques well known to those skilled in the art, including, but not limited to, injection (e.g., sterile aqueous solution or dispersion), sterile powder, external preparation, and the like.

According to the present invention, the pharmaceutical composition may further comprise a pharmaceutically acceptable carrier which is widely used in pharmaceutically manufacturing techniques. For example, the pharmaceutically acceptable carrier can comprise one or more reagents selected from the group consisting of solvent, buffer, emulsifier, suspending agent, decomposer, disintegrating agent, dispersing agent, binding agent, excipient, stabilizing agent, chelating agent, diluent, gelling agent, preservative, wetting agent, lubricant, absorption delaying agent, liposome, and the like. The selection and quantity of these reagents fall within the scope of the professional literacy and routine techniques of those skilled in the art.

According to the present invention, the pharmaceutically acceptable carrier comprises a solvent selected from the group consisting of water, normal saline, phosphate buffered saline (PBS), aqueous solution containing alcohol, and combinations thereof.

According to the present invention, the pharmaceutical composition can be administered by parenteral routes selected from the group consisting of subcutaneous injection, intraepidermal injection, intradermal injection, and intralesional injection.

According to the present invention, the pharmaceutical composition can be manufactured to an external preparation suitable for topical application to the skin using techniques well known to those skilled in the art, including, but not limited to, emulsion, coagulation, gel, ointment, cream, patch, liniment, powders, aerosol, spray, lotion, serum, paste, foam, drop, suspension, salve, and bandage.

According to the present invention, the external preparation is prepared by mixing the pharmaceutical composition of the present invention with a base well known to those skilled in the art.

According to the present invention, the base may comprise one or more additives selected from the group consisting of water, alcohols, glycol, hydrocarbons such as petroleum jelly and white petrolatum, wax such as paraffin and yellow wax, preserving agents, antioxidants, surfactants, absorption enhancers, stabilizing agents, gelling agents such as Carbopol® 974P, microcrystalline cellulose and carboxymethylcellulose, active agents, humectants, odor absorbers, fragrances, pH adjusting agents, chelating agents, emulsifiers, occlusive agents, emollients, thickeners, solubilizing agents, penetration enhancers, anti-irritants, colorants, and propellants. The selection and quantity of these additives fall within the scope of professional literacy and routine techniques of those skilled in the art.

According to the present invention, the cosmetic composition can further comprise an acceptable adjuvant that is widely used in the manufacture of cosmetic compositions. For example, the acceptable adjuvant may comprise one or more reagents selected from the group consisting of solvents, gelling agents, active agents, preservatives, antioxidants, screening agents, chelating agents, surfactants, coloring agents, thickening agents, fillers, fragrances, and odor absorbers. The selection and quantity of these reagents fall within the scope of professional literacy and routine techniques of those skilled in the art.

According to the present invention, the cosmetic composition can be manufactured to a form suitable for skincare or makeup using techniques well known to those skilled in the art, including, but not limited to, aqueous solution, aqueous-alcohol solution or oily solution, oil-in-water type, water-in-oil type or composite type emulsion, gel, ointment, cream, mask, patch, pack, liniment, powders, aerosol, spray, lotion, serum, paste, foam, dispersion, drop, mousse, sunblock, tonic water, foundation, makeup remover products, soap, and other body cleansing products.

According to the present invention, the cosmetic composition may also be used in combination with one or more external use agents with known activities selected from the group consisting of whitening agents such as tretinoin, catechin, kojic acid, arbutin and vitamin C, humectants, anti-inflammatory agents, bactericides, ultraviolet absorbers, plant extracts extracts such as aloe extract, skin nutrients, anesthetics, anti-acne agents, antipruritics, analgesics, antidermatitis agents, antihyperkeratolytic agents, anti-dry skin agents, antipsoriatic agents, antiaging agents, anti-wrinkle agents, antiseborrheic agents, wound-healing agents, corticosteroids, and hormones. The selection and quantity of these external use agents fall within the scope of professional literacy and routine techniques of those skilled in the art.

According to the present invention, the food product can be used as a food additive, added by the conventional method in the preparation of the raw material, or added during the preparation of food, and prepared with any edible material into food products for human and non-human animals.

According to the present invention, types of food products include, but not limited to, beverages, fermented foods, bakery products, health foods, and dietary supplements.

Example 1

1.1 Preparation of Fermentation Product of *Punica granatum* as Food Product

First, the *Punica granatum* juice and water were mixed at a ratio of 1:5 to 1:10 (w/w), and extracted at 50° C.-100° C. for 0.5-3 hours to obtain a *Punica granatum* extract. The *Punica granatum* extract was cooled to room temperature for subsequent three-stage fermentation. The three-stage fermentation is that the *Punica granatum* extract was sequentially inoculated with 0.01-0.5% *Saccharomyces cerevisiae* BCRC 20271 and fermented at 25-35° C. for 1-2 days; 0.01-0.25% *Lactobacillus plantarum* TCI028 (BCRC 910805) and fermented at 25-35° C. for 1-3 days; 1-20% *Acetobacter aceti* BCRC 11688 (the above strains were all purchased from the Biosource Collection and Research Center (BCRC) of the Food Industry Research and Development Institute (FIRDI), Taiwan) and fermented at 25-35° C. for 14-21 days. Thereafter, the obtained mixture was concentrated under reduced pressure at 45° C. to 70° C., and filtered through a 200 to 400-mesh strainer. 0.5-1.5% citric acid and 40-70% isomaltooligosaccharide were added to adjust the format, and then sterilized to obtain the fermentation product of *Punica granatum* as a food product (i.e., a second fermentation product of *Punica granatum*).

1.2 Preparation of Fermentation Product of *Punica granatum* as Cosmetic Composition First, the *Punica granatum* juice and water were mixed at a ratio of 1:5 to 1:10 (w/w), and extracted at 50° C.-100° C. for 0.5-3 hours to obtain a *Punica granatum* extract. The *Punica granatum* extract was cooled to room temperature for subsequent fermentation. The fermentation is that the *Punica granatum* extract was sequentially inoculated with 0.01-0.5% *Saccharomyces cerevisiae* BCRC 20271 and fermented for 1-2 days; 0.01-0.25% *Lactobacillus plantarum* TCI028 (BCRC 910805) and fermented for 1-3 days. Thereafter, the obtained mixture was concentrated under reduced pressure at 45° C. to 70° C., and filtered through a filter bag having a pore size of 0.5 to 20 μm. The obtained filtrate was sterilized at 90 to 120° C. for 30 to 120 minutes, and then 0.5 to 1.5% phenoxyethanol (as a preservative) was added to obtain the fermentation product of *Punica granatum* as a cosmetic composition (i.e., a first fermentation product of *Punica granatum*).

Example 2

Total Polyphenol Content Detection of Fermentation Product of *Punica* granatum

First, a standard solution was prepared. 10 g of gallic acid was dissolved in water and a volume of 10 mL was added to the volumetric flask. 0 μL/mL, 20 μL/mL, 40 μL/mL, 60 μL/mL, 80 μL/mL, and 100 μL/mL standard solutions were prepared, respectively, and 100 μL of each standard solution was added to a 10 mL centrifuge tube. Thereafter, 500 μL of Folin-Ciocalteu's phenol reagent was added, mixed and let stand for 3 minutes, and 400 μL of 7.5% sodium carbonate was added, mixed and let stand for 30 minutes. 200 μL of each reaction solution was transferred to a 96-well plate, and the absorbance was measured at 750 nm.

In addition, the fermentation product of *Punica granatum* as the food product obtained in Example 1 was used as an experimental group, and the *Punica granatum* extract was used as a comparative group. The experimental group and the comparative group were diluted with water, respectively, and a volume of 100 mL was added to an eppendorf tube. Thereafter, 500 μL of Folin-Ciocalteu's phenol reagent was added, mixed and let stand for 3 minutes, and 400 μL of 7.5% sodium carbonate was added, mixed and let stand for 30 minutes. 200 μL of each reaction solution was transferred to a 96-well plate, and the absorbance was measured at 750 nm. The result of this example is shown in FIG. 1.

FIG. 1 is a schematic diagram showing the total polyphenol content detection of the fermentation product of *Punica granatum* of the present invention. As shown in FIG. 1, compared with the comparative group, the total polyphenol content of the experimental group is significantly increased (by 2.6-fold). The result of Example 2 indicates that the fermentation product of *Punica granatum* of the present invention releases a large amount of total polyphenols.

Example 3

Antiglycative Activity Analysis of Fermentation Product of *Punica* Granatum

First, the fermentation product of *Punica granatum* as the food product obtained in Example 1 was used as an experimental group, and the *Punica granatum* extract was used as a comparative group. 0.25 mL of the appropriately diluted samples of the experimental group and the comparative group were taken, respectively, and 0.25 mL of bovine serum albumin (BSA) (60 mg/mL BSA containing 0.06% $NaN_3$ was prepared with 200 mM sodium phosphate buffer (pH 7.4)) solution and a fructose solution (1.5 M D-fructose in 200 mM sodium phosphate buffer) were added and mixed evenly. Subsequently, the volume of 0.1 mL was taken to measure the fluorescence value using the excitation light at 360 nm and the emission light at 460 nm, and it is the zero point before the reaction. A volume of 0.45 mL was taken and cultured at 50° C. for 24 hours, and then a volume of 0.1 mL was taken to measure the fluorescence value, which is the end point of the reaction. The control group was replaced with an equal amount of sample dissolution solvent, and an equal amount of 3 mM aminoguanidine (AG) was used as a positive control group. The antiglycative activity (%) was calculated by the following formula (1):

$$\text{Antiglycative activity (\%)} = \left[1 - \frac{\text{Fluorescence sample}_{24hr} - \text{Fluorescence sample}_{0hr}}{\text{Fluorescence control}_{24hr} - \text{Fluorescence control}_{0hr}}\right] \times 100\%. \quad (1)$$

Figure 2:
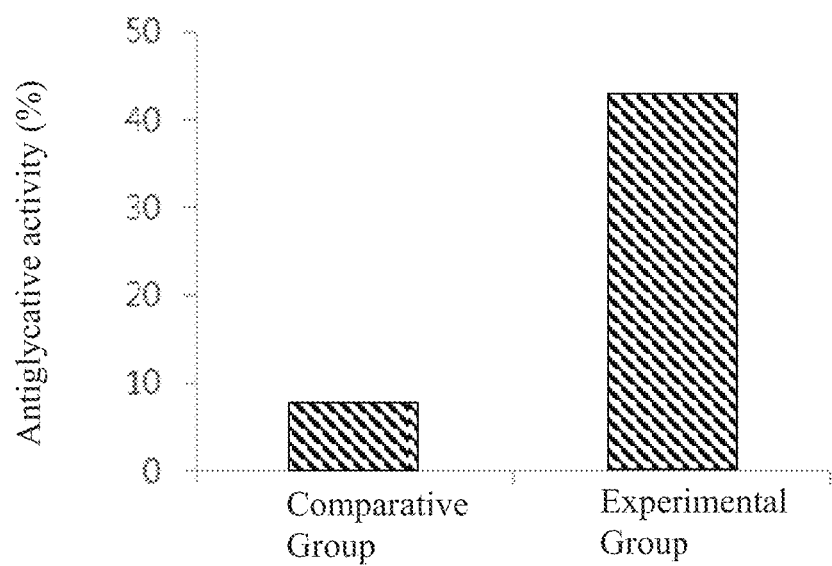
FIG. 2 is a schematic diagram showing the antiglycative activity analysis of the fermentation product of *Punica granatum* of the present invention.

The result of this example is shown in FIG. 2. FIG. 2 is a schematic diagram showing the antiglycative activity analysis of the fermentation product of *Punica granatum* of the present invention. As shown in FIG. 2, compared with the comparative group, the antiglycative activity of the experimental group is significantly increased (by 35%). The result of Example 3 indicates that the fermentation product of *Punica granatum* of the present invention has excellent antiglycative activity.

Example 4

Evaluation of Effect of Fermentation Product of *Punica granatum* on Resisting and Defending Against UVA First, the human skin fibroblast CCD-966Sk (ATCC® CRL-1881) was cultured in minimum essential medium supplemented with 10% fetal bovine serum (FBS), 1% penicillin/streptomycin and 1 mM sodium pyruvate (Gibco). 200 μL of the medium was added to each well of a 96-well culture plate to have $5 \times 10^3$ human skin fibroblasts per well. After 24 hours of incubation at 37° C., the medium was removed.

Thereafter, four groups of human skin fibroblasts (i.e., an experimental group, a comparative group, a UVA group and a control group) were prepared. The cells in the experimental group, the comparative group and the UVA group were irradiated with UVA for 1 hour at a dose of 15 $J/cm^2$ using a UV irradiation chamber, which caused a lethal dose 50% ($LD_{50}$), indicating that radiation dose of 50% cell death. 0.5% fermentation product of *Punica granatum* as the food product was added to the cells in the experimental group, 0.5% *Punica granatum* extract was added to the cells in the comparative group, and the cells in the UVA group were left untreated. The cells in the control group were not irradiated with UVA.

After cell cultures in each group were cultured in a 37° C. incubator for 24 hours, 15 μL of 3-[4,5-dimethylthiazol-2-yl]-2,5-diphenyltetrazolium bromide (MTT, 4 mg/mL in PBS) was added per well, followed by culturing at 37° C. for 4 hours. Thereafter, the medium in each well was removed, 50 μL of DMSO (ECHO/DA1101-000000-72EC) was added to each well to decompose the formazan crystal, and then the plate was placed in a shaker, followed by incubation for 10 minutes. The absorbance at 570 nm ($OD_{570}$) in each well was measured using an ELISA reader (BioTek).

The cell viability (%) was calculated by substituting the absorbance ($OD_{570}$) into the following formula (2):

Cell viability (%)=($OD_{570}$ of each group/$OD_{570}$ of control group)×100%　　(2).

Statistically significant differences between each group were determined by the Student's t-test. The result of this example is shown in FIG. 3.

Figure 3:
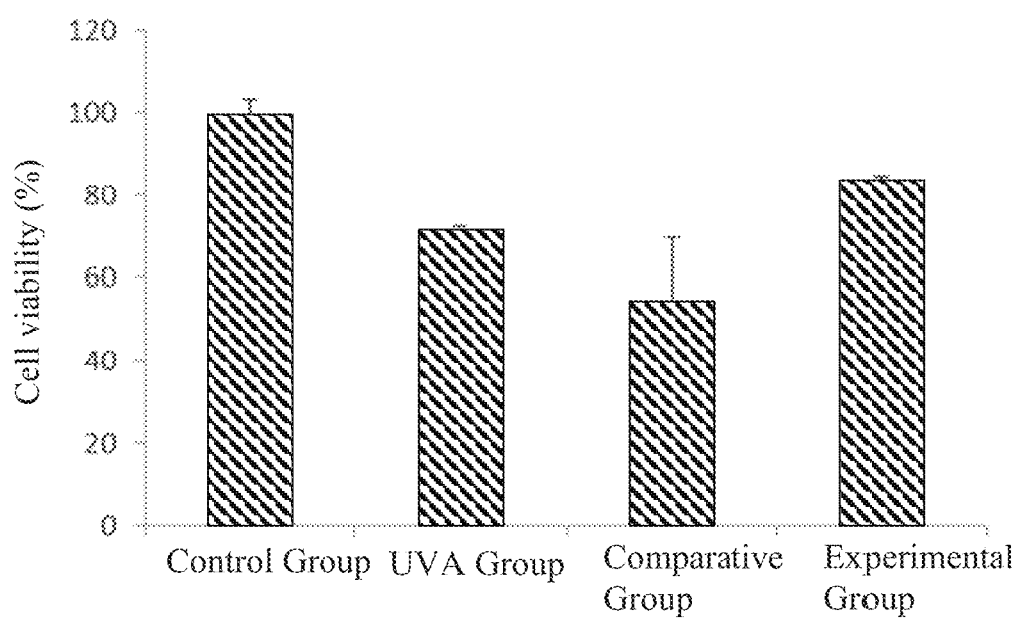
FIG. 3 is a schematic diagram showing the effect of the fermentation product of *Punica granatum* of the present invention on the ability to resist and defend against UVA.

FIG. 3 is a schematic diagram showing the effect of the fermentation product of *Punica granatum* of the present invention on the ability to resist and defend against UVA. As shown in FIG. 3, compared with the control group, the cell viability (%) of the UVA group is reduced, indicating that irradiation of UVA to human skin fibroblasts causes cell death. Compared with the UVA group and the comparative group, the cell viability (%) of the experimental group is significantly increased (the cell viability of the experimental group is increased by 12% compared with that of the UVA group). The result of Example 4 indicates that the fermentation product of *Punica granatum* of the present invention has the effect on resisting and defending against UVA.

Example 5

Evaluation of Effect of Fermentation Product of *Punica granatum* on Inhibition of Melanogenesis First, the mouse skin melanoma cell line B16F10 (ATCC CRL-6475) was cultured in Dulbecco's Modified Eagle's Medium (DMEM) supplemented with 1% penicillin/streptavidin (Gibco) and 10% FBS (Gibco). 3 mL of the medium was added to each well of a 6-well culture plate to have 1.5×10⁵ B16F10 cells per well. After 24 hours of incubation at 37° C., the medium was removed.

Thereafter, three groups of B16F10 cells (i.e., an experimental group, a comparative group and a control group) were prepared. 0.5% fermentation product of *Punica granatum* as the food product (containing 3 mL of DMEM) was added to the cells in the experimental group, 2% *Punica granatum* extract (containing 3 mL of DMEM) was added to the cells in the comparative group, and DMEM was added to the cells in the control group.

After cell cultures in each group were cultured at 37° C. for 48 hours, the medium was removed and washed twice with 1×PBS (Gibco). Trypsin was added to treat the cells for 3 minutes and the suspended cells were collected in a 15 mL centrifuge tube, followed by spinning at 400×g/5 minutes to precipitate the cells. After rinsing twice with 1×PBS, the cell pellet was resuspended with 200 µL of 1×PBS. The cell solution was placed in liquid nitrogen for 10 minutes, and then left standing at room temperature for 30 minutes for thawing. After thawing was complete, rotation was performed at 12,000×g for 30 minutes, and the supernatant was removed and 120 µL of 1 N NaOH (in dd$H_2O$). After mixing evenly, the mixture was left standing in a dry bath at 60° C. for 1 hour. Thereafter, 100 µL of the mixture was taken into a 96-well culture plate, and the absorbance at 450 nm ($OD_{450}$) in each well was measured using an ELISA reader.

The melanin content (%) was calculated by substituting the absorbance ($OD_{450}$) into the following formula (3):

Melanin content (%)=($OD_{450}$ of each group/$OD_{450}$ of control group)×100%　　(3).

Statistically significant differences between each group were determined by the Student's t-test. The result of this example is shown in FIG. 4.

Figure 4:
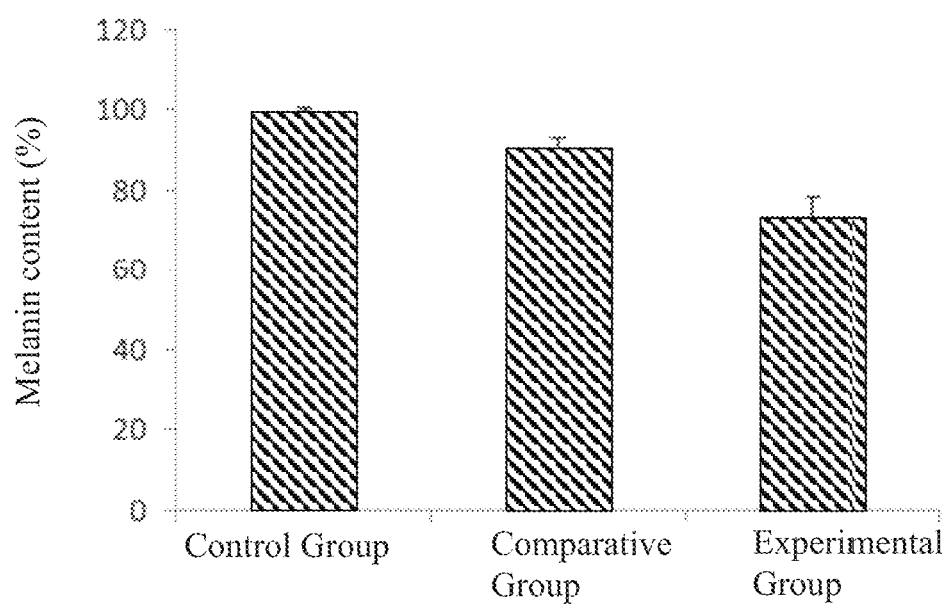
FIG. 4 is a schematic diagram showing the effect of the fermentation product of *Punica granatum* of the present invention on inhibiting melanin production.

FIG. 4 is a schematic diagram showing the effect of the fermentation product of *Punica granatum* of the present invention on inhibiting melanin production. As shown in FIG. 4, compared with the control group and the comparative group, the melanin content of the experimental group is significantly reduced (compared with the control group, the melanin content of the experimental group is reduced by 20%). The result of Example 5 indicates that the fermentation product of *Punica granatum* of the present invention has the effect on inhibiting melanin production.

Example 6

Evaluation of Effect of Fermentation Product of *Punica granatum* on Anti-Inflammation First, the mouse macrophage RAW 264.7 (ATCC TIB-71) was cultured in 90% DMEM supplemented with 10% FBS (Gibco), 1% penicillin/streptomycin (Gibco) and 4 mM L-glutamine (Gibco). 200 µL of the medium was added to each well of a 96-well culture plate to have 2.5×10⁴ cells per well. After incubating for 24 hours in a constant temperature incubator at 37° C., 5% $CO_2$, the medium was removed.

Thereafter, four groups of RAW 264.7 cells (i.e., an experimental group, a comparative group, an LPS group and a control group) were prepared. 200 ng/mL lipopolysaccharide (LPS)(Sigma; SI-L2880-25MG) was added to the cells in the LPS group, the comparative group and the experimental group to induce the inflammatory reaction. 1 mg/mL fermentation product of *Punica granatum* as the food product was added to the cells in the experimental group, 1% *Punica granatum* extract was added to the cells in the comparative group, the cells in the LPS group were left untreated, and the cells in the control group were not added with LPS and left untreated. The LPS group, the experimental group and the comparative group were prepared in a medium containing no FBS, and one sample was subjected to four repetitions.

After cell cultures in each group were reacted for 24 hours, 150 µL of the culture solution was taken out from each well and placed in a new 96-well culture plate, followed by adding 130 µL of secondary water. Thereafter, the Griess reagent kit (Life technologies; 1445263) was used to prepare the Griffith reagent (the ratio of reagent A to reagent B was 1:1), and 20 µL of the Griffith reagent was incubated with the medium in the 96-well culture plate for 30 minutes in the dark. The absorbance at 548 nm ($OD_{548}$) in each well was measured using a microplate reader. In particular, the higher the absorbance, the higher the concentration of NO. Statistically significant differences between each group were determined by the Student's t-test. The result of this example is shown in FIG. 5.

Figure 5:
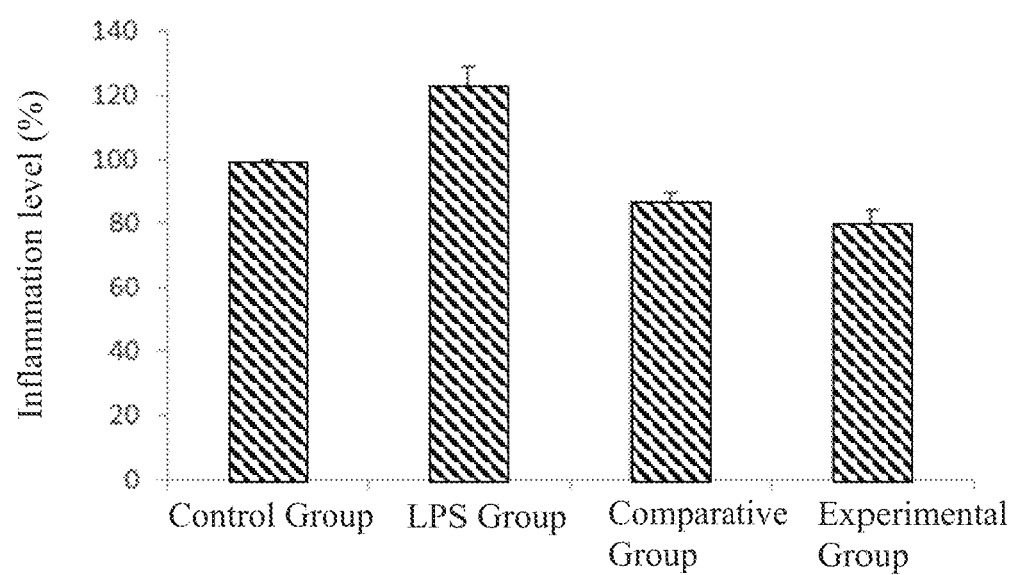
FIG. 5 is a schematic diagram showing the effect of the fermentation product of *Punica granatum* of the present invention on anti-inflammation.

FIG. 5 is a schematic diagram showing the effect of the fermentation product of *Punica granatum* of the present invention on anti-inflammation. As shown in FIG. 5, compared with the comparative group, the inflammation level of the LPS group is increased, indicating that LPS induces an inflammatory response in RAW 264.7 cells. Compared with the LPS group and the comparative group, the inflammation level of the experimental group is significantly reduced (compared with the LPS group, the inflammation level of the experimental group is reduced by 43%). The result of Example 6 indicates that the fermentation product of *Punica granatum* of the present invention has the anti-inflammatory effect.

Example 7

Evaluation of Effect of Fermentation Product of *Punica granatum* on Enhancing Skin Firmness First, the human skin fibroblast CCD-966Sk (BCRC 60153) was cultured in Eagle minimum essential medium (EMEM), formulated in Earle's Balanced Salt Solution (Earle's BSS), supplemented with 0.1 mM non-essential amino acid, 1.5 g/L sodium bicarbonate, 1 mM sodium pyruvate (90%) and 10% FBS (Gibco). The medium was added to each well of a 24-well culture plate to have $2 \times 10^5$ cells per mL of medium per well.

Thereafter, three groups of human skin fibroblasts (i.e., an experimental group, a comparative group, and a control group) were prepared. 0.5% fermentation product of *Punica granatum* as the cosmetic composition according to Example 1.2 was added to the cells in the experimental group, 0.5% *Punica granatum* extract was added to the cells in the comparative group, and the cells in the control group were left untreated. 0.66 volumes of a well-mixed cell suspension (±experimental variable) was added to a sterile tube, and 0.33 volumes of a 3 mg/mL collagen solution was added to the cell suspension. The appropriate volume of 1M NaOH was quickly added, and the solution was mixed up and down 3 times, wherein the least amount of NaOH needed to turn the phenol red media indicator a light pink color will produce the most rigid collagen gels. 500 µL of the mixture was immediately transferred to a 1.9-cm$^2$ well to allow gels to solidify and cover at room temperature for 20 minutes.

Subsequently, a minimum of an equal volume (500 µL) of culture media (±experimental variable) was gently added to each well, and the gel was dissociated from its mold by gently running the tip of a 200-µL pipet tip along gel edges being careful not to shear or tear gels. The gels were resuspended by gently pulling the edges of the gel away from the mold using the pipet tip, and the plate was gently swirled to make sure that gel was free from the plate. Thereafter, the 24-well plate was replaced into an incubator at 37° C., humidified 5% $CO_2$.

At predetermined time-points, the 24-well plate was removed from the incubator for image acquisition. The 24-well plate was placed on top of a lightbox, a digital camera was used at a fixed distance above the gels, and an image was obtained at each of the time-points. The gels were returned to the incubator. Subsequently, images can be analyzed with ImageJ software, the outline of each collagen gel was traced and the surface area was calculated according to ImageJ software instructions, followed by reporting the surface area at each time point as a percentage of initial gel surface area. The result of this example is shown in FIG. 6.

Figure 6:
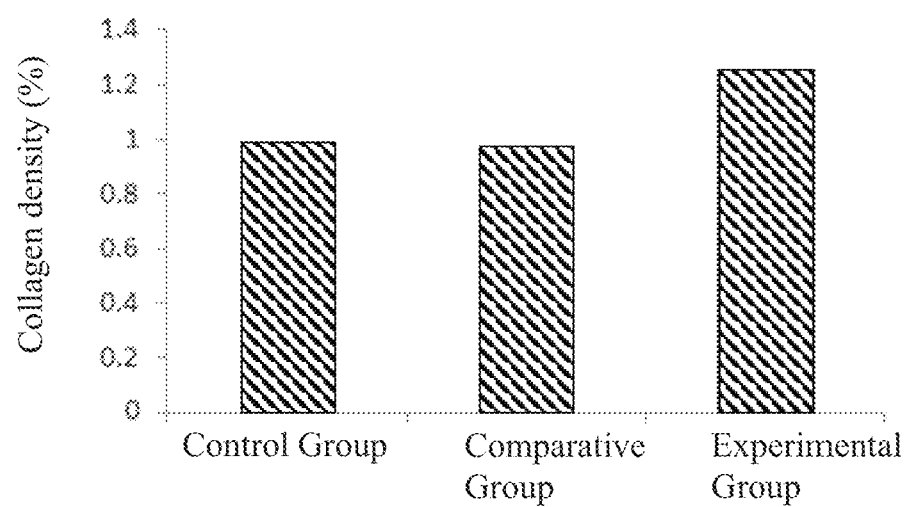
FIG. 6 is a schematic diagram showing the effect of the fermentation product of *Punica granatum* of the present invention on elevating the degree of skin firmness.

FIG. 6 is a schematic diagram showing the effect of the fermentation product of *Punica granatum* of the present invention on elevating the degree of skin firmness. As shown in FIG. 6, compared with the control group and the comparative group, the collagen density (%) of the experimental group is significantly increased (compared with the control group, the collagen density of the experimental group is increased by 25%). The result of Example 7 indicates that the fermentation product of *Punica granatum* of the present invention has the effect on enhancing the skin firmness by increasing the collagen density.

Example 8

Evaluation of Effect of Fermentation Product of *Punica granatum* on Regulating Gene Expression Related to Skin Elasticity In this example, the fermentation product of *Punica granatum* was investigated whether it can achieve the effect on enhancing skin elasticity by regulating the gene expression related to skin elasticity.

First, the human skin fibroblast CCD-966Sk was cultured in the MEM medium supplemented with 10% FBS, 1 mM sodium pyruvate and 1% penicillin/streptomycin. The concentration was $2 \times 10^5$ cells/well, followed by incubation at 37° C. for 24 hours, and the medium was removed.

Thereafter, three groups of the cultured cells (i.e., a control group, a comparative group, and an experimental group) were prepared. 0.25% fermentation product of *Punica granatum* as the cosmetic composition according to Example 1.2 was added to the cells in the experimental group, 0.25% *Punica granatum* extract was added to the cells in the comparative group, and the cells in the control group were left untreated. Subsequently, the cell cultures in each group were harvested and subjected to gene expression analysis.

In this example, genes related to skin elasticity include the matrix metalloproteinase 2 (MMP2) gene, the tissue inhibitor of matrix metalloproteinase 1 (TIMP1) gene, and the collagen type IV alpha 4 chain (COL4A4) gene.

RNA extraction was performed using an RNA extraction kit (Geneaid). 2,000 ng of the RNA in each group thus obtained was taken and the extracted RNA was reverse transcribed into cDNA by SuperScript® III reverse transcriptase (Invitrogen). The cDNA was used as a template, primer pairs for amplification of target genes, including MMP2, TIMP1, COL4A4, and GAPDH (as internal control) were used, and their nucleotide sequences are shown in Table 1. The quantification of target genes was measured by quantitative real-time PCR using KAPA CYBR FAST qPCR kit (2×) (KAPA Biosystems) carried out in ABI Step One Plus Real-Time PCR system (ABI). The melting curves of the PCR product were analyzed during the quantitative real-time PCR.

TABLE 1

| Target gene | SEQ ID NO.# | Primer name | Sequence (5' → 3') |
|---|---|---|---|
| MMP2 | SEQ ID NO.1 | MMP2-F | GATACCCCTTTGACGGTAAGGA |
|  | SEQ ID NO.2 | MMP2-R | CCTTCTCCCAAGGTCCATAGC |
| TIMP1 | SEQ ID NO.3 | TIMP1-F | AGAGTGTCTGCGGATACTTCC |
|  | SEQ ID NO.4 | TIMP1-R | CCAACAGTGTAGGTCTTGGTG |
| GAPDH | SEQ ID NO.5 | GAPDH-F | CTGGGCTACACTGAGCACC |
|  | SEQ ID NO.6 | GAPDH-R | AAGTGGTCGTTGAGGGCAATG |
| COL4A4 | SEQ ID NO.7 | COL4A4-F | AGATAAGGGTCCAACTGGTGT |
|  | SEQ ID NO.8 | COL4A4-R | ACCTTTAACGGCACCTAAAATGA |

The relative quantification of gene expression was determined by using the $2^{-\Delta\Delta C_t}$ method. The relative fold change was calculated using cycle threshold ($C_T$) of GAPDH as internal control and the mock group as reference genes following the formula:

$$\Delta C_T = C_{T_{target/ref}} - C_{T_{internal\ control}}$$

$$\Delta\Delta C_T = \Delta C_{T_{target}} - \Delta C_{T_{ref}}$$

$$\text{Fold change} = 2^{-\Delta\Delta C_T\ mean}$$

Figure 8:
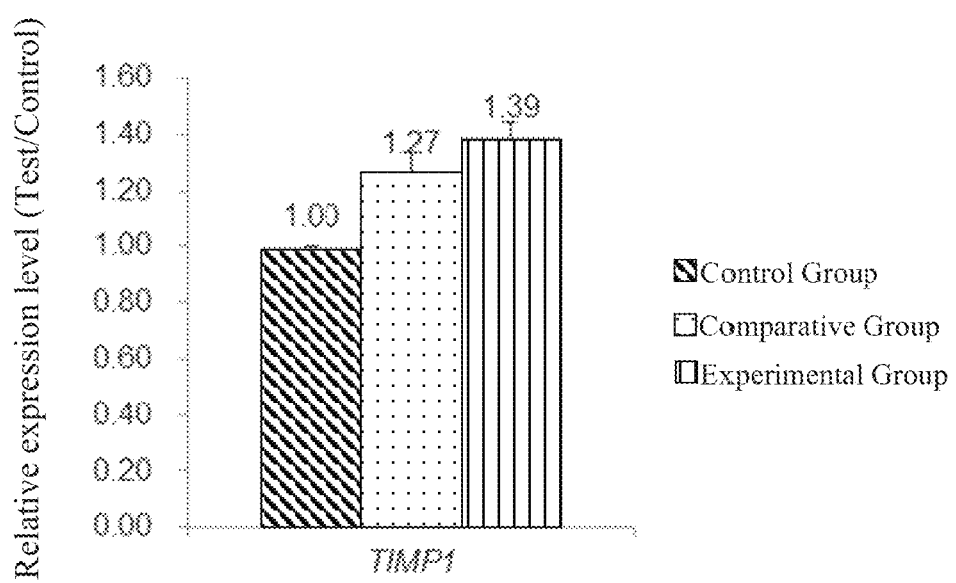
FIG. 8 is a schematic diagram showing the effect of the fermentation product of *Punica granatum* of the present invention on regulating the expression of TIMP1 gene.
Figure 9:
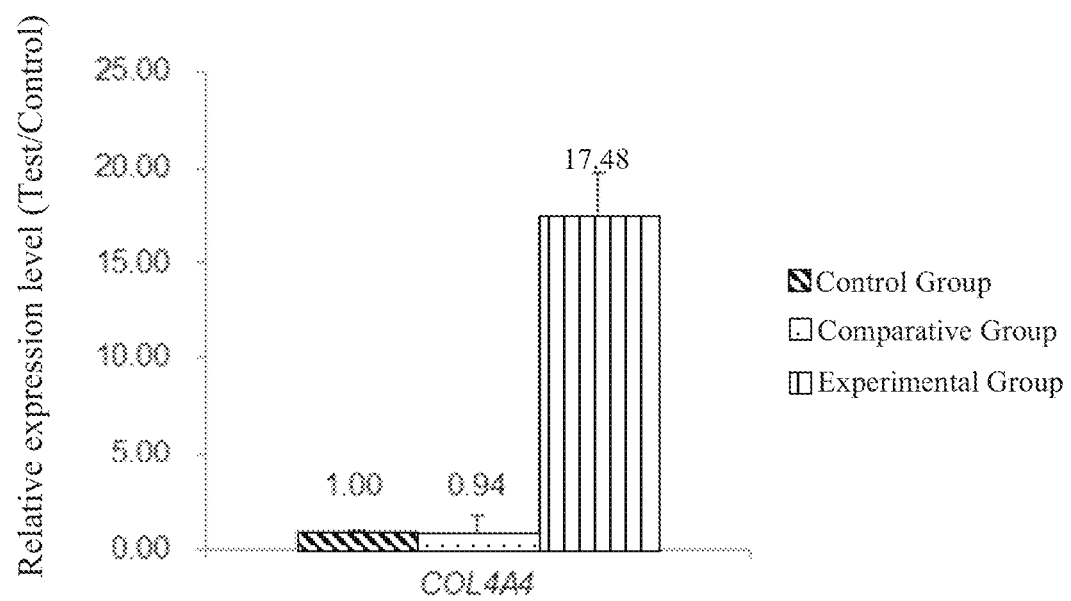
FIG. 9 is a schematic diagram showing the effect of the fermentation product of *Punica granatum* of the present invention on regulating the expression of COL4A4 gene.

For instance, the $\Delta C_T$ of COL4A4 was calculated by subtraction of $C_T$ of COL4A4 and $C_T$ of GAPDH. Then the $\Delta\Delta C_T$ of COL4A4 was the difference of $\Delta C_T$ of the test sample and mock. Finally, the relative fold of COL4A4 of the test sample is 2 to the power of minus average of $\Delta\Delta C_T$. The standard deviation of the relative fold change was calculated by STDEV in Excel. The expression level of the target gene in the control group was used as a comparative standard of 1. The statistical significance was performed by using the single-tailed Student's t-test in Excel. The results of this example are shown in FIGS. 7-9.

Figure 7:
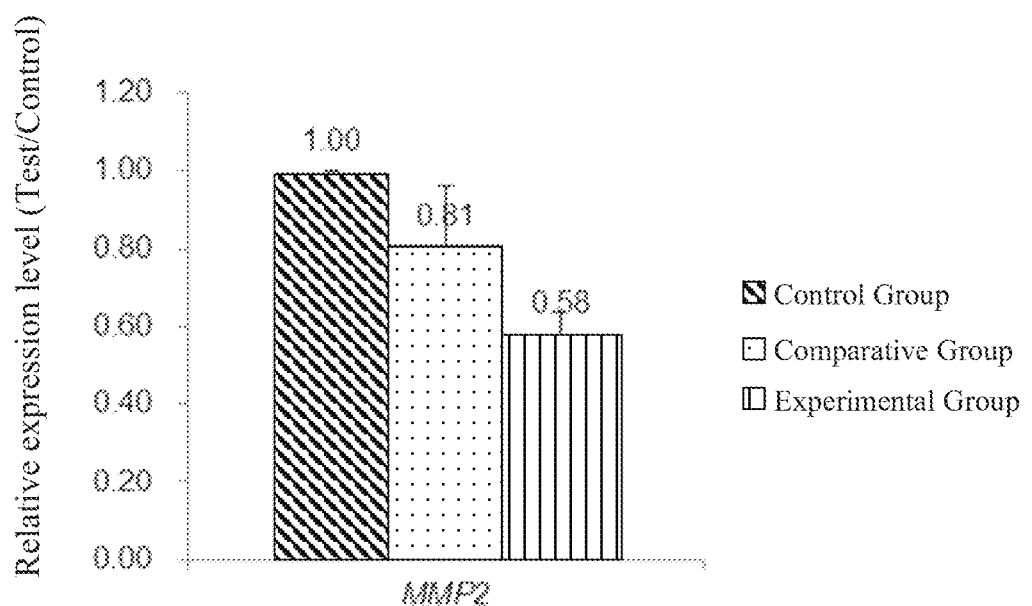
FIG. 7 is a schematic diagram showing the effect of the fermentation product of *Punica granatum* of the present invention on regulating the expression of MMP2 gene.

FIG. 7 is a schematic diagram showing the effect of the fermentation product of *Punica granatum* of the present invention on regulating the expression of MMP2 gene. FIG. 8 is a schematic diagram showing the effect of the fermentation product of *Punica granatum* of the present invention on regulating the expression of TIMP1 gene. FIG. 9 is a schematic diagram showing the effect of the fermentation product of *Punica granatum* of the present invention on regulating the expression of COL4A4 gene. As shown in FIG. 7, regarding the MMP2 gene, the relative expression ratio of the experimental group is significantly lower than that of the control group and the comparative group (the relative expression ratio of the experimental group is reduced by 42% compared with that of the control group), indicating that the fermentation product of *Punica granatum* of the present invention can prevent collagen from being degraded by inhibiting the expression level of the MMP2 gene. As shown in FIG. 8, regarding the TIMP1 gene, compared with the control group and the comparative group, the relative expression ratio of the experimental group is significantly increased (compared with the control group, the relative expression ratio of the experimental group is increased by 39%), indicating that the fermentation product of *Punica granatum* of the present invention can inhibit collagen decomposing gene activity by increasing the expression level of the TIMP1 gene. As shown in FIG. 9, regarding the COL4A4 gene, compared with the control group and the comparative group, the relative expression ratio of the experimental group is significantly increased (compared with the control group, the relative expression ratio of the experimental group is increased by 17 folds), indicating that the fermentation product of *Punica granatum* of the present invention can promote collagen production by increasing the expression level of the COL4A4 gene. The result of Example 8 indicates that the fermentation product of *Punica granatum* of the present invention can achieve the effect on enhancing skin elasticity by regulating the gene expression related to skin elasticity.

Example 9

Human Body Function Test of Fermentation Product of *Punica granatum* as Food Product In this example, the fermentation product of *Punica granatum* as the food product according to Example 1.1 was used to examine whether it has the effect on improving the human skin.

Figure 11:
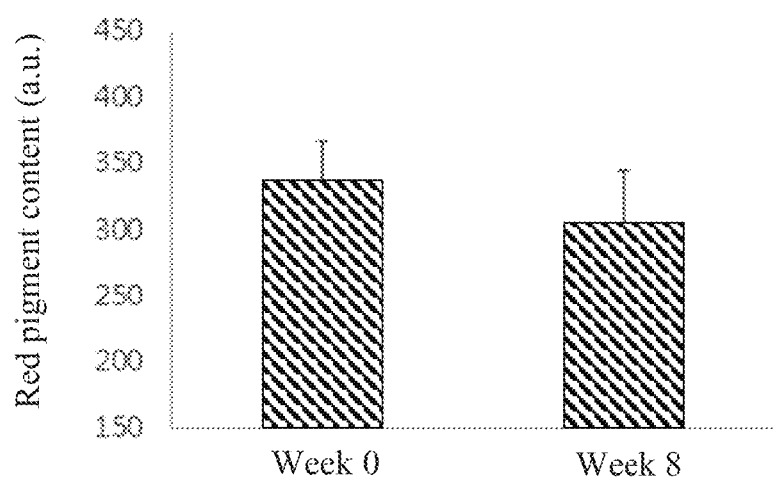
FIG. 11 is a schematic diagram showing the effect of the fermentation product of *Punica granatum* of the present invention on reducing the production of red pigment in humans.
Figure 12:
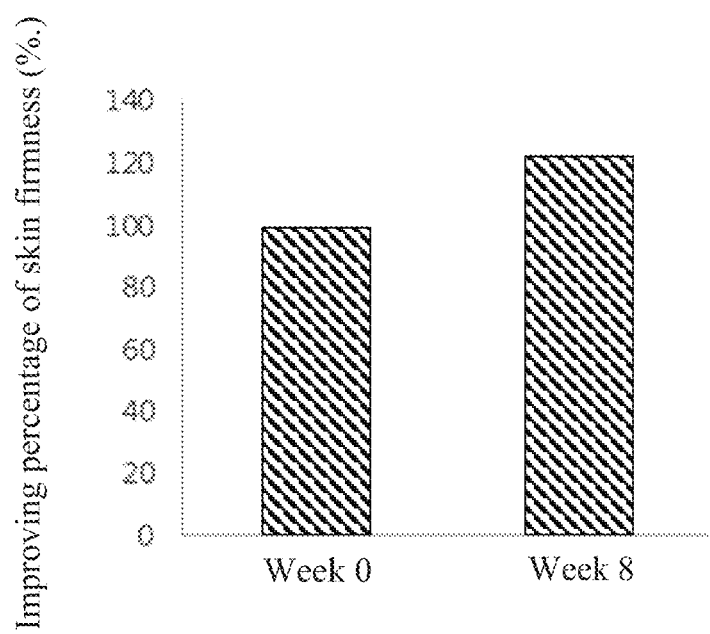
FIG. 12 is a schematic diagram showing the effect of the fermentation product of *Punica granatum* of the present invention on improving the firmness of human skin.

First, eight 25-year-old to 45-year-old office workers were recruited, and each subject was asked to orally drink 10 mL of 15-30% fermentation product of *Punica granatum* as the food product every day for 8 weeks. The test items include melanin content, red pigment content, and improving percentage of skin firmness before and after drinking, and the tests were performed using the VISIA Complexion Analysis System (Canfield Scientific, USA). The results of this example are shown in FIGS. 10-12.

Figure 10:
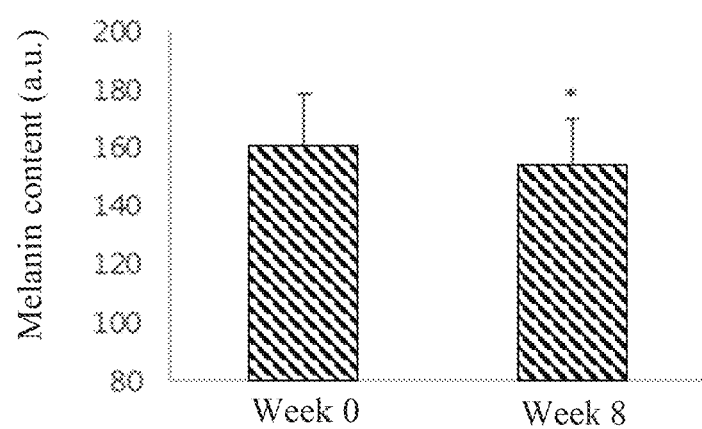
FIG. 10 is a schematic diagram showing the effect of the fermentation product of *Punica granatum* of the present invention on inhibiting melanin production in humans, wherein "*" indicates p<0.05 when compared with week 0.

FIG. 10 is a schematic diagram showing the effect of the fermentation product of *Punica granatum* of the present invention on inhibiting melanin production in humans. FIG. 11 is a schematic diagram showing the effect of the fermentation product of *Punica granatum* of the present invention on reducing the production of red pigment in humans FIG. 12 is a schematic diagram showing the effect of the fermentation product of *Punica granatum* of the present invention on improving the firmness of human skin. As shown in FIG. 10, compared with before drinking (week 0), the subjects have a significant decrease in melanin content at week 8 after drinking (compared with week 0, the melanin content of the subjects is reduced by 4.1% at week 8 after drinking). As shown in FIG. 11, compared with before drinking (week 0), the subjects have a significant decrease in red pigment content at week 8 after drinking (compared with week 0, the red pigment content of the subjects is reduced by 10.3% at week 8 after drinking). As shown in FIG. 12, compared with before drinking (week 0), the improving percentage of skin firmness of the subjects measured at week 8 after drinking is increased (compared with week 0, the improving percentage of skin firmness of the subjects measured at week 8 after drinking is increased by 22.2%). The result of Example 9 indicates that the fermentation product of *Punica granatum* as the food product has the effect on improving the human skin.

Example 10

Human Body Function Test of Fermentation Product of *Punica granatum* as Cosmetic Composition In this example, the fermentation product of *Punica granatum* as the cosmetic composition according to Example 1.2 was used to examine whether it has the effect on improving the human skin.

Figure 14:
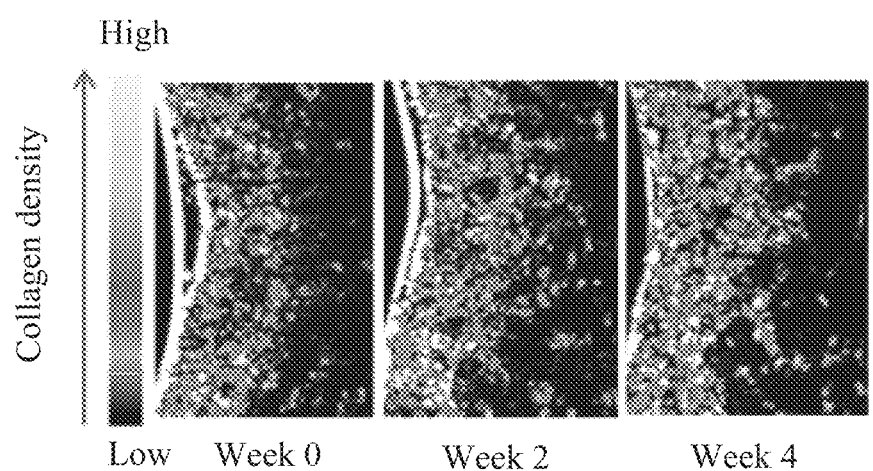
FIG. 14 is an image drawing showing the effect of the fermentation product of *Punica granatum* of the present invention on increasing the human collagen density.
Figure 15:
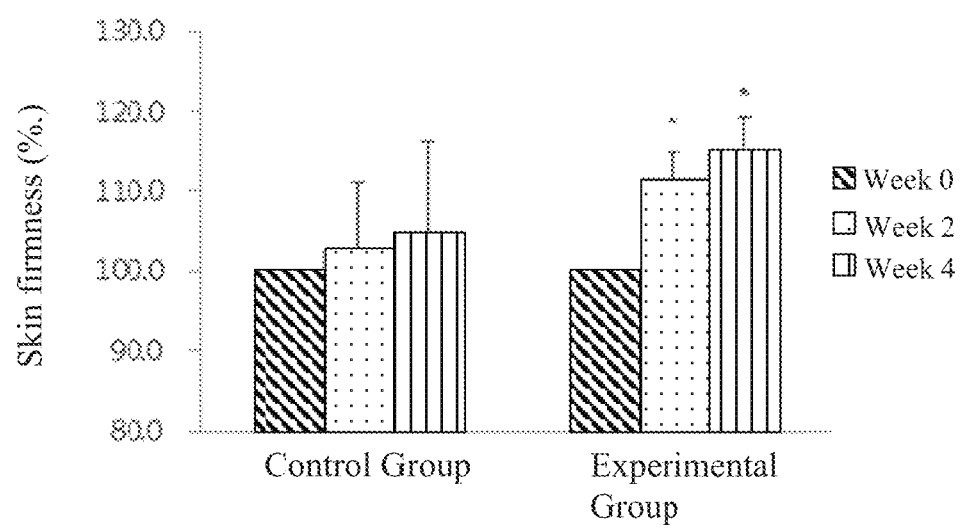
FIG. 15 is a schematic diagram showing the effect of the fermentation product of *Punica granatum* of the present invention on improving the firmness of human skin, wherein "*" indicates p<0.05 when compared with week 0.

First, 8 subjects were recruited, the left face of each subject was used as a control group, and the right face was used as an experimental group. After cleaning the face every morning and evening, the placebo was applied to the skin of the control group, and 5-15% fermentation product of *Punica granatum* as the cosmetic composition was applied to the skin of the experimental group. The massage was promoted by a slight massage on the fingertips, and the test was performed before use (week 0) and at week 2 and week 4 after use. The test items include collagen density, skin looseness and skin wrinkles, and the tests were performed using the VISIA Complexion Analysis System (Canfield Scientific, USA). The results of this example are shown in FIGS. 13-15.

Figure 13:
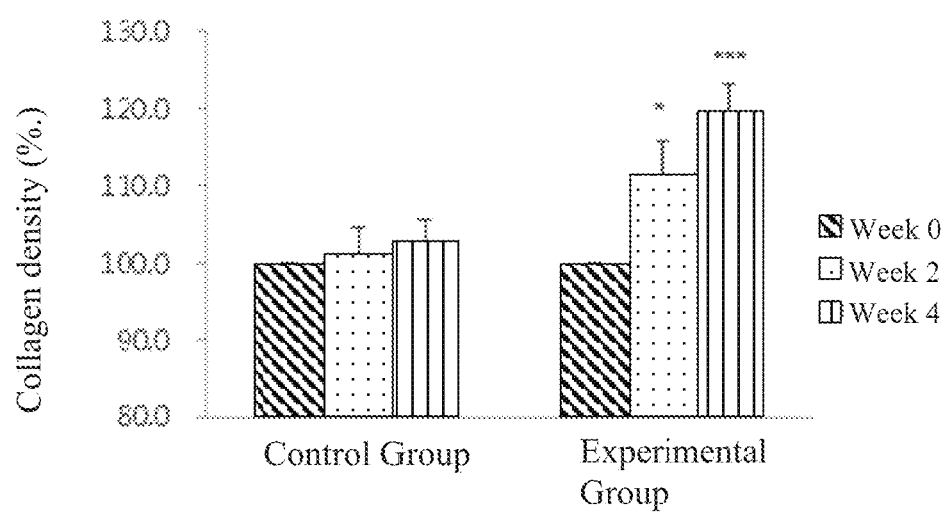
FIG. 13 is a schematic diagram showing the effect of the fermentation product of *Punica granatum* of the present invention on increasing the human collagen density, wherein "*" indicates p<0.05 when compared with week 0; and "***" indicates p<0.001 when compared with week 0.

FIG. 13 is a schematic diagram showing the effect of the fermentation product of *Punica granatum* of the present invention on increasing the human collagen density. FIG. 14 is an image drawing showing the effect of the fermentation product of *Punica granatum* of the present invention on increasing the human collagen density. FIG. 15 is a schematic diagram showing the effect of the fermentation product of *Punica granatum* of the present invention on improving the firmness of human skin. As shown in FIG. 13, compared with week 0, the skin collagen density of the experimental group is increased significantly with time, while the control group is not. Compared with week 2, the skin collagen density of the experimental group is increased by 11.6% at week 2 after use, and the skin collagen density of the experimental group is increased by 19.6% at week 4 after use. As shown in FIG. 14, compared with week 0, the skin collagen density of the experimental group is increased with time. The less black part in FIG. 14, the higher the collagen density. As shown in FIG. 15, compared with week 0, the skin firmness of the experimental group is increased significantly with time, while the control group is not. Compared with week 0, the skin firmness of the experimental group is increased by 11.6% at week after use, and the skin firmness of the experimental group is increased by 15% at week 4 after use. The result of Example 10 indicates that the fermentation product of Punica granatum as the cosmetic composition has the effect on improving the human skin.

In summary, the fermentation product of Punica granatum has the effect on regulating the expression of the MMP gene, the TIMP gene and the COL4A4 gene, releasing total polyphenols of the Punica granatum by the microbial fermentation process, increasing the antioxidant and skin care functions, promoting collagen production, reducing pigment production and accumulation, enhancing skin firmness, improving skin darkness, anti-aging and smoothing wrinkles.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A method for regulating expression of matrix metalloproteinase (MMP) gene, tissue inhibitor of matrix metalloproteinase (TIMP) gene, and collagen type IV alpha 4 chain (COL4A4) gene, comprising administering to a subject in need thereof a composition comprising an effective amount of a fermentation product of *Punica granatum*, and the fermentation product of *Punica granatum* obtained by a process comprising the following steps:
   (a) extracting the *Punica granatum* with water to obtain a *Punica granatum* extract;
   (b) sequentially fermenting the *Punica granatum* extract with *Saccharomyces* cerevisiae and *Lactobacillus* plantarum to obtain a first fermentation product of *Punica granatum*;
   wherein the *Saccharomyces* cerevisiae has a concentration ranging, from 0.01% to 0.5%, and the *Lactobacillus* plantarum has a concentration ranging from 0.01% to 0.25%; and
   (c) fermenting the first fermentation product of *Punica granatum* with *Acetobacter aceti* to obtain the fermentation product of *Punica granatum*, wherein the *Acetobacter aceti* has a concentration ranging from 1% to 20%.

2. The method according to claim 1, wherein the composition is in the form of a pharmaceutical composition, a food product, or a cosmetic composition.

3. The method according to claim 1, wherein the MMP, gene is MMP2 gene.

4. The method according to claim 1, wherein the TIMP gene is TIMP1 gene.

5. A method for promoting collagen production and anti-aging, comprising administering to a subject in need thereof a composition comprising an effective amount of a fermentation product of *Punica granatum*, and the fermentation product of *Punica granatum* obtained by a process comprising the following steps:
   (a) extracting the *Punica granatum* with water to obtain a *Punica granatum* extract;
   (b) sequentially fermenting the *Punica granatum* extract with *Saccharomyces* cerevisiae and *Lactobacillus plantarum* to obtain a first fermentation product of *Punica granatum*;
   wherein the *Saccharomyces* cerevisiae has a concentration ranging from 0.01% to 0.5%, and the *Lactobacillus* plantarum has a concentration ranging from 0.01% to 0.25%; and
   (c) fermenting the first fermentation product of *Punica granatum* with *Acetobacter aceti* to obtain the fermentation product of *Punica granatum*, wherein the *Acetobacter aceti* has a concentration ranging from 1% to 20%.

6. Me method according to claim 5, wherein the composition is in the form of the cosmetic composition.

7. The method according to claim 5, wherein the composition is in the form of the food product.

* * * * *